United States Patent [19]

Schaper et al.

[11] 4,289,660

[45] Sep. 15, 1981

[54] PERFUME COMPOSITIONS CONTAINING TRICYCLO[5.2.1.$0^{2.6}$]DECANE CARBOXYLIC ACID ESTERS

[75] Inventors: Ulf-Armin Schaper, Düsseldorf; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 170,914

[22] Filed: Jul. 21, 1980

Related U.S. Application Data

[63] Continuation of Ser. No. 65,606, Aug. 10, 1979.

[30] Foreign Application Priority Data

Aug. 12, 1978 [DE] Fed. Rep. of Germany ....... 2835445

[51] Int. Cl.$^3$ ........................... A61K 7/46; C11B 9/00

[52] U.S. Cl. ................................ 252/522 R; 560/117

[58] Field of Search .............. 252/522 R; 260/429 CY

[56] References Cited

U.S. PATENT DOCUMENTS

| | | | |
|---|---|---|---|
| 2,688,627 | 9/1954 | Cohen et al. | 260/429 CY |
| 3,598,745 | 8/1971 | Dunkel | 252/522 R |
| 3,679,749 | 7/1972 | Grossman et al. | 252/522 R |
| 3,786,075 | 1/1974 | Teisseire et al. | 252/522 R |

FOREIGN PATENT DOCUMENTS 2249376 4/1973 Fed. Rep. of Germany ... 252/522 R

OTHER PUBLICATIONS

Chem. Absts. vol. 49, #12541e (1956).

*Primary Examiner*—John F. Niebling

*Attorney, Agent, or Firm*—Hammond & Littell, Weissenberger and Muserlian

[57] ABSTRACT

This invention is directed to perfume compositions comprising esters of mixtures of tricyclo[5.2.1.$0^{2.6}$]-decane carboxylic acids of the general formulas:

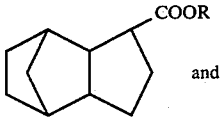

(I)

and

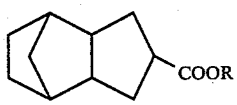

(II)

wherein R represents a saturated or unsaturated linear or branched aliphatic hydrocarbon radical having from about 1 to 5 carbon atoms; as well as the use of the compositions as odorants.

3 Claims, No Drawings

PERFUME COMPOSITIONS CONTAINING TRICYCLO[5.2.1.0$^{2.6}$]DECANE CARBOXYLIC ACID ESTERS

This is a continuation of Ser. No. 65,606, filed Aug. 10, 1979.

BACKGROUND OF THE INVENTION

Certain esters of tricyclo[5.2.1.0$^{2.6}$]decane-3/4-carboxylic acids are known and have been described in the literature. See, for example, U.S. Pat. No. 2,688,627 (Standard Oil) ref. Chem. Abstr. 49, 12 541e and J. Gen. Chem. UdSSR 31, 1324 (1961) wherein the methyl and ethyl esters have been described. However, applicants have surprisingly discovered that these methyl and ethyl esters, as well as previously unknown unsaturated aliphatic esters, are useful as perfuming agents in perfume compositions.

OBJECTS OF THE INVENTION

It is an object of this invention to provide perfuming agents and perfume compositions having characteristic fragrances and excellent adhesion.

It is also an object of this invention to provide perfuming agents and perfumery compositions comprising esters of mixtures of tricyclo[5.2.1.0$^{2.6}$]decane-3/4-carboxylic acids.

It is a further object of this invention to provide unsaturated aliphatic esters of mixtures of tricyclo[5.2.1.0$^{2.6}$]decane-3/4-carboxylic acids.

These and other objects of the invention will become more apparent in the discussion below.

DESCRIPTION OF THE INVENTION

It has been found that esters of mixtures of tricyclo[5.2.1.0$^{2.6}$]decane carboxylic acids of the general formulas

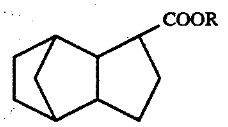

(I)

and (II)

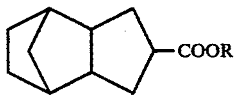

wherein R represents a saturated or unsaturated linear or branched aliphatic hydrocarbon radical having from about 1 to 5 carbon atoms, constitute valuable new perfuming agents which can be used to advantage as perfuming agents in compositions for perfuming technical and cosmetic preparations. Useful perfume compositions comprise from about 1 to 50 percent by weight, based on the total weight of the perfume compositions of the esters of mixtures of tricyclo[5.2.1.0$^{2.6}$-decane-3/4-carboxylic acids, i.e., esters of mixtures of tricyclo[5.2.1.0$^{2.6}$]decane-3-carboxylic acid and tricyclo[5.2.1.0$^{2.6}$]decane-4carboxylic acid.

The radical R can represent a saturated or unsaturated linear or branched aliphatic hydrocarbon radical having from about 1 to 5 carbon atoms. More particularly, these are alkyls having 1 to 5 carbon atoms, alkenyl having 3 to 5 carbon atoms and alkynyls having 3 to 5 carbon atoms. Mixtures of esters of Formulas I and II wherein R is an unsaturated hydrocarbon radical are of interest, and mixtures of esters wherein R represents the allyl radical $-CH_2-CH=CH_2$ or the propargyl radical $-CH_2-C\equiv CH$, are of particular interest. The perfuming agents and perfume compositions of this invention can also be comprised of more than one mixture of esters of Formulas I and II. For example, a useful perfuming agent or perfumery composition may comprise a mixture of esters of Formulas I and II wherein R is an allyl radical as well as a mixture of said esters wherein R is a propargyl radical.

The preparation of the esters to be used according to the invention can be effected according to generally known esterification methods by reacting tricyclo[5.2.1.0$^{2.6}$]decane-3/4-carboxylic acids, or their acid chlorides, with alcohols corresponding to the desired R radical in the presence of condensing agents, such as $P_2O_5$. The mixture of the acids can be obtained by hydroformylation of tricyclo[5.2.1.0$^{2.6}$]dec-3-ene with subsequent oxidation, corresponding to the following reaction scheme:

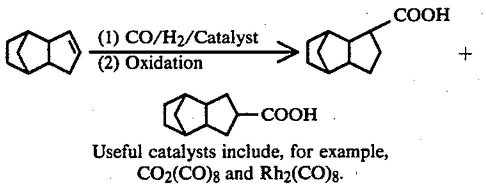

(III)

Useful catalysts include, for example, $Co_2(CO)_8$ and $Rh_2(CO)_8$.

The mixture of tricyclo[5.2.1.0$^{2.6}$]decane-3/4-carboxylic acids obtained in this manner is available commercially as the product known under the name TCD-Carboxylic Acid S (from Hoechst AG).

Another method of preparing the esters to be used according to the invention on their underlying acids comprises the carbonylation reactions according to Reppe or Koch. The reaction takes place according to the following scheme:

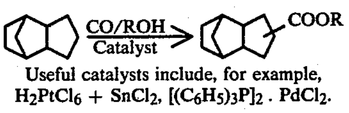

(IV)

Useful catalysts include, for example, $H_2PtCl_6 + SnCl_2$, $[(C_6H_5)_3P]_2 \cdot PdCl_2$.

If the reaction is carried out in alcohol instead of in an aqueous medium, the corresponding esters are obtained directly. The acids or esters obtained are, as with reaction scheme III, a mixture of different stereoisomers of the tricyclo[5.2.1.0$^{2.6}$]decane-3/4-carboxylic acids or their esters. This mixture is not separated, and the mixture comprises the perfuming agent to be used according to the invention.

The esters of the mixtures of tricyclo[5.2.1.0$^{2.6}$]-decane-3/4-carboxylic acids to be used according to the invention are valuable perfuming agents having characteristic aromas. They can be easily combined to new and interesting aromas. The allyl and propargyl esters are of particular importance because of their special aromas. The propargyl esters have an interesting meaty-walnut aroma, while the allyl esters have an ocimene-styrolyl aroma. These aromas are particularly suitable for the development of novel perfume compositions.

One advantage of the perfuming agents, or perfumes, of this invention is that they are distinguished by particularly intensive and lasting fragrances of high quality and fullness. Other advantages are that the perfuming agents can be combined very satisfactorily to form perfume compositions and novel fragrances and that they also have a high degree of adherence.

The esters of the mixtures of the tricyclo[5.2.1.$0^{2.6}$]-decane-$\frac{3}{4}$-carboxylic acids to be used according to the invention can be mixed with other perfumes in various quantitative ratios to form new perfume compositions. In general, the esters of the mixture of the tricyclo[5.2.1.$0^{2.6}$]decane-$\frac{3}{4}$-carboxylic acids in the perfume composition will comprise from about 1 to 50 percent by weight, based on the total weight of the perfuming composition. The remainder of the composition is comprised of conventional perfumery constituents. Perfume compositions of this type can be used directly as a perfume or, alternatively, for perfuming cosmetics, such as creams, lotions, toilet waters, aerosols, mouthwashes, toilet soaps, technical articles, such as detergents and cleansers, disinfectants, and textile finishing agents, and the like.

The following examples are intended to explain further the subject of the invention, but without limiting the invention to these examples.

EXAMPLE 1

Production of Tricyclo[5.2.1.$0^{2.6}$]decane-$\frac{3}{4}$-Carboxylic Propargyl Ester An amount of TCD Carboxylic Acid S, which comprises a mixture of tricyclo[5.2.1.$0^{2.6}$]decane-$\frac{3}{4}$-carboxylic acids, was reacted with an equimolar amount of propargyl alcohol in the presence of a condensing agent, $P_2O_5$.

The product, which was recovered by fractionation in vacuo, was found to have a boiling point of 100° to 110° C./0.013 m bar and a refractive index of $n_D^{20}=1.506$.

The product was distinguished by a meaty-walnut aroma that was intensive and had long adherence.

In a similar manner the following additional compounds were produced:

(1) Tricyclo[5.2.1.$0^{2.6}$]decane-$\frac{3}{4}$-carboxylic, Allyl Ester B.P.=74°-81° C. (0.07 m bar); refractive index of $n_D^{20}=1.497$; ocimene-styrolyl aroma.

(2) Tricyclo[5.2.1.$0^{2.6}$]decane-$\frac{3}{4}$-carboxylic, Ethyl Ester B.P.=60°-63° C. (0.013 m bar); refractive index of $n_D^{20}=1.489$ (Literature: B.P.=103° C. [4 m bar] and refractive index of $n_D^{20}=1.486$); fruity, marmalade aroma.

(3) Tricyclo[5.2.1.$0^{2.6}$]decane-$\frac{3}{4}$-carboxylic, n-Propyl Ester B.P.=94°-100° C. (0.013 m bar); refractive index of $n_D^{20}=1.488$; technical meaty aroma.

(4) Tricyclo[5.2.1.$0^{2.6}$]decane-$\frac{3}{4}$-carboxylic, Isopropyl Ester B.P.=67°-72° C. (0.07 m bar); refractive index of $n_D^{20}=1.483$; raspberry aroma.

(5) Tricyclo[5.2.1.$0^{2.6}$]decane-$\frac{3}{4}$-carboxylic, n-Butyl Ester B.P.=78°-80° C. (0.07 m bar); refractive index of $n_D^{20}=1.484$; slightly fruity aroma.

(6) Tricyclo[5.2.1.$0^{2.6}$]decane-$\frac{3}{4}$-carboxylic, t-Butyl Ester B.P.=92°-95° C. (0.07 m bar); refractive index of $n_D^{20}=1.481$; slightly fruity aroma.

The following represent examples of perfume compositions:

EXAMPLE 2

Hyacynth Complex

| Component | Parts by weight |
|---|---|
| Tricyclo[5.2.1.$0^{2.6}$]decane-$\frac{3}{4}$ carboxylic, aklyl ester | 100.0 |
| Cis-$\beta$-hexhenyl acetate | 200.0 |
| Dimethylbenzylcarbinyl acetate | 120.0 |
| Cinnamic alcohol | 100.0 |
| Linelool | 100.0 |
| Geraniol | 100.0 |
| Methyljonone | 80.0 |
| Terpineol | 70.0 |
| Styrax oil | 60.0 |
| Citronellol | 50.0 |
| Galbanum oil | 20.0 |
| | 1,000.0 |

EXAMPLE 3

Chypre Base

| Component | Parts by Weight |
|---|---|
| Tricyclo[5.2.1.$0^{2.6}$]decane-$\frac{3}{4}$-carboxylic, propargyl ester | 100.0 |
| Bergamotte oil | 440.0 |
| Linalool | 150.0 |
| Coumarin | 90.0 |
| Oak moss absolute | 50.0 |
| Isobutyl quinoline | 50.0 |
| Linalyl acetate | 50.0 |
| Vetiver oil | 20.0 |
| Sandalwood oil | 10.0 |
| Mandarin oil | 10.0 |
| Patchouli oil | 10.0 |
| Lavender oil | 10.0 |
| Tonka absolute | 10.0 |
| | 1,000.0 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfume composition comprising as a perfume from about 1 to 50 percent by weight of an isomeric mixture of tricyclo[5.2.1.$0^{2.6}$]decane carboxylic acids of the general formulas

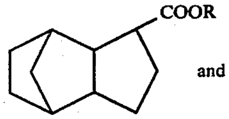

(I)

and

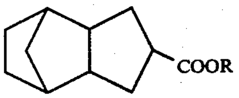

(II)

wherein R represents a saturated or unsaturated linear or branched aliphatic hydrocarbon radical having from about one to five carbon atoms, the remainder comprising customary constituents including at least one other fragrance substance.

2. The perfume composition of claim 1 wherein R represents an allyl or propargyl radical.

3. The perfume composition of claim 1 comprising an effective amount of a mixture of esters wherein R represents an allyl radical and a mixture of esters wherein R represents a propargyl radical.

* * * * *